US010456787B2

(12) United States Patent
Blankenstein et al.

(10) Patent No.: US 10,456,787 B2
(45) Date of Patent: Oct. 29, 2019

(54) REAGENT COMPONENT DISPENSING CAPS FOR REAGENT CONTAINERS USED IN AUTOMATED CLINICAL ANALYZERS

(71) Applicant: Instrumentation Laboratory Company, Bedford, MA (US)

(72) Inventors: Gert Blankenstein, Dortmund (DE); Hansong Zeng, Lowell, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

(21) Appl. No.: 15/234,111

(22) Filed: Aug. 11, 2016

(65) Prior Publication Data

US 2018/0043363 A1 Feb. 15, 2018

(51) Int. Cl.

| | |
|---|---|
| ***B01L 3/00*** | (2006.01) |
| ***B65D 39/08*** | (2006.01) |
| ***B65D 51/28*** | (2006.01) |
| ***G01N 35/10*** | (2006.01) |

(52) U.S. Cl.

CPC .............. *B01L 3/523* (2013.01); *B65D 39/08* (2013.01); *B65D 51/2807* (2013.01); *B01L 2200/025* (2013.01); *B01L 2200/0689* (2013.01); *B01L 2200/16* (2013.01); *B01L 2300/042* (2013.01); *B01L 2300/0832* (2013.01);

(Continued)

(58) Field of Classification Search

CPC ............... B01L 3/523; B01L 2200/025; B01L 2200/0689; B01L 2200/16; B01L 2300/042; B01L 2300/044; B01L 2300/047; B01L 2300/0672; B01L 2300/0832; B01L 2300/123; B01L 2400/0478; B65D 39/08; B65D 51/2807; B65D 51/2835; B65D 51/2864; B65D 51/2892; B65D 81/3211; G01N 35/1002

USPC .......................................................... 422/550

See application file for complete search history.

(56) References Cited

U.S. PATENT DOCUMENTS 4,793,475 A * 12/1988 Itzel .................. B65D 51/2814 206/219
4,898,293 A * 2/1990 Morel ................. B65D 51/225 206/222
5,114,411 A 5/1992 Haber et al.

(Continued)

FOREIGN PATENT DOCUMENTS

EP 2110332 10/2009
EP 2399564 A1 12/2011

(Continued)

OTHER PUBLICATIONS

International Searching Authority, International Search Report and Written Opinion, International Application No. PCT/US2017/045695, dated Oct. 26, 2017.

(Continued)

*Primary Examiner* — Benjamin R Whatley

(74) *Attorney, Agent, or Firm* — Burns & Levinson, LLP; Joseph P. Quinn

(57) ABSTRACT

Described is an automated reagent dispensing cap and methods of use in an automated clinical analyzer for introducing one or more reagent components housed in the reagent dispensing cap into a container enclosing another reagent component with which it is combined to achieve a reagent useful for diagnostic testing.

8 Claims, 6 Drawing Sheets

10 100 42 21 20 50 12 40 44 REAGENT PART 1 24 62 75 22 23 REAGENT PART 2 60 72

(52) U.S. Cl.
CPC . *B01L 2300/123* (2013.01); *B01L 2400/0478* (2013.01); *G01N 35/1002* (2013.01)

(56) References Cited

U.S. PATENT DOCUMENTS

| | | | | |
|---|---|---|---|---|
| 5,250,440 | A * | 10/1993 | Kelln | G01N 35/025 356/246 |
| 5,525,299 | A * | 6/1996 | Lowe | B01L 3/50825 206/219 |
| 6,132,400 | A * | 10/2000 | Waldenburg | A61M 5/19 604/191 |
| 6,527,110 | B2 | 3/2003 | Moscovitz | |
| 6,533,113 | B2 * | 3/2003 | Moscovitz | B65D 51/2835 206/222 |
| 7,017,735 | B2 | 3/2006 | Carlson | |
| 9,051,099 | B2 | 6/2015 | Salinas | |
| 9,102,441 | B1 | 8/2015 | Orvik | |
| 2008/0121591 | A1 * | 5/2008 | Knight | C12M 47/06 436/178 |
| 2009/0308831 | A1 | 12/2009 | Anderson | |
| 2010/0000341 | A1 * | 1/2010 | Hasegawa | A61B 10/0038 73/864 |
| 2010/0044377 | A1 | 2/2010 | Porter | |
| 2010/0089860 | A1 | 4/2010 | Wiggins et al. | |
| 2012/0183956 | A1 * | 7/2012 | Ross | G01N 1/44 435/6.1 |
| 2013/0331298 | A1 | 12/2013 | Rea | |
| 2015/0038876 | A1 * | 2/2015 | Gonzalez-Zugasti | A61B 5/1411 600/583 |
| 2015/0076170 | A1 | 3/2015 | Goettke | |

FOREIGN PATENT DOCUMENTS

| | | |
|---|---|---|
| EP | 2647584 | 10/2013 |
| WO | 2007003001 | 1/2007 |
| WO | 2007/062745 | 6/2007 |
| WO | 2015151252 | 10/2015 |
| WO | 2016/087626 | 6/2016 |

OTHER PUBLICATIONS

International Preliminary Report on Patentability for PCT Application No. PCT/US2017/045695, dated Feb. 21, 2019.

* cited by examiner 10
50
12
40
44
60
62
72

10
50
12
40
44
62
30
60
64
22
72

10
50
43
30
44
22
72

REAGENT COMPONENT DISPENSING CAPS FOR REAGENT CONTAINERS USED IN AUTOMATED CLINICAL ANALYZERS

TECHNICAL FIELD OF THE INVENTION

The present invention is related to in-vitro diagnostic (IVD) testing procedures. More specifically, the present invention provides reagent component dispensing caps for reagent containers for storing and mixing reagent components of reagents used in diagnostic tests and conducted in an automated clinical analyzer. The present invention also provides methods of use of the reagent dispensing caps.

BACKGROUND

Currently available in-vitro diagnostic (IVD) testing procedures are encumbered with numerous steps that involve manual interventions before a reagent can be prepared for use in a liquid and/or powder format. For instance, in a diagnostic testing lab, before using the reagents for sample testing, typically patient body fluids such as whole blood, plasma, serum, urine, cerebrospinal fluid and the like, a medical worker collects different reagent components from separate vials/bottles, uses a pipette to pipette diluents with a certain volume to the vial of powdered reagents or to the vial with concentrated liquid reagents, waits for a certain time for reconstitution, and finally mixes the reagents manually by shaking, stirring, or rotating, for example. This manual process reduces the speed in which a diagnostic test is completed, increases the risk of human error and operator contamination with potentially toxic chemicals, and raises the cost of packaging.

In addition to the above mentioned drawbacks in the preparation of the reagents, the reagent components in a reagent container (e.g., a vial or a bottle) are susceptible to evaporation when the reagent container is placed in a clinical analyzer. Evaporation of reagent(s) compromise the consistency of the reagent's stability and wastes reagents. More importantly, evaporation of reagents compromises the consistency in results generated by the clinical analyzer and the results are unreliable. Therefore, there is a need to improve on reagent containers for storing and mixing components of reagents for use in diagnostic tests that are conducted in an automated clinical analyzer. There is also a need to improve on the reagent preparation process and to improve on the usage efficiency of the reagent containers for IVD applications in an automated clinical analyzer. A reagent packaging solution that addresses these disadvantages is described below.

SUMMARY OF INVENTION

Described herein is a reagent packaging solution with multi-component storage, automated reconstitution and mixing of the stored components, and evaporation prevention of the stored components.

In one aspect, the invention is directed to a device for storing and dispensing reagent components in an automated clinical analyzer. The device according to this aspect of the invention comprises a housing having a first end and an adjacent first opening, a second end and an adjacent second opening, and internal threads extending along at least a portion of an internal surface of the housing. The housing defines a chamber with a lumen positioned between the housing first and second ends. A cylindrical member positioned at the first end of the housing comprises a first end and a second end. The cylindrical member has external threads for mating with at least the internal threads of the housing. The cylindrical member is rotatable on the internal threads of the housing and translatable from the first end of the housing towards the second end of said housing. In one embodiment of this aspect of the invention, a seal is positioned across the lumen of the second end of the chamber between the second end of the housing and the second end of the cylindrical member.

In one embodiment of this aspect of the invention, the device includes a reagent component positioned in the lumen of the chamber between the seal and the second end of the cylindrical member. In one embodiment, an actuator is operably positioned at the first end of the cylindrical member. The actuator may feature a ram, a needle, or the rotatable cylindrical member.

In various embodiments of this aspect of the invention, the device includes a seal that may be integral with and joined to the second end of the cylindrical member. An attachment piece may be positioned at the second end of the housing for mating to a container. The attachment piece in various embodiments may consist of threads, snap-lock, mating rings, receiving grooves, a friction-fit mechanism, Luer lock, or one or more tabs. A plurality of external threads for mating with the container may be positioned on the external surface of the first end of the housing. The device may further feature a cap for reversibly sealing the first opening of the housing.

In another aspect, the invention is directed to a device for storing and dispensing reagents, comprising a housing having a long axis, a first end, and an adjacent first opening, and a second end and an adjacent second opening. The housing defines a chamber having a lumen positioned between the first and second ends, and a deformable member positioned across the lumen of the chamber. The deformable member includes a piercing probe including a pointed tip positioned on the side of the deformable membrane that is closest to the second end of the housing. In this aspect of the invention, a seal for sealing the lumen of the chamber is positioned in the lumen of the chamber between the second end of the housing and the tip of the piercing probe. A chamber for storing reagents is positioned between the seal and the deformable member. The device according to this aspect of the invention includes an attachment piece at the second end of said housing for mating to a container. The attachment piece may be a snap-lock mechanism, friction-fit mechanism, threads, one or more tabs, receiving grooves, mating rings, and a Luer lock, or one or more grooves. The device according to this aspect of the invention may further feature a cap for reversibly sealing the first opening of the housing and a ram for actuating the device.

In another aspect the invention is directed to a device for storing and dispensing reagents, comprising a cylindrical housing as described above and a plug positioned and laterally slideable in the lumen of the chamber. The plug defines a through hole in the plug that is parallel to the long axis of the housing. The through hole includes a reservoir for storing a substance such as a reagent component. The substance is released from the reservoir when the through hole is aligned with the lumen of the chamber. The device according to this aspect of the invention includes an attachment piece at the second end of the housing for mating to a container. The attachment piece in various embodiments is a snap-lock mechanism, friction-fit mechanism, threads, one or more tabs, receiving grooves, mating rings, a Luer lock, or one or more tabs.

In another aspect, the invention is directed to a method for storing reagent components in a reagent dispensing cap and automated mixing of reagent components to prepare a diagnostic reagent in an automated clinical analyzer according to the various embodiments of the device described herein.

DESCRIPTION

Described below is an automated reagent dispensing cap for separately storing and automatically dispensing at least one stored component to be combined with another stored component to make a reagent used in diagnostic assays, and methods for dispensing the stored component when used in an automated clinical analyzer, including hemostasis analyzers, immunoassay analyzers, chemistry analyzers, and the like. The stored reagent component(s) (i.e., one or more of the reagent components) is housed in the reagent dispensing cap freely, or in a primary pack such as a pouch, blister pack, pill, bag, using a membrane (e.g., a pierceable membrane) or in an ampoule containing one or more reagent components. The stored reagent components can be in a liquid form (e.g., a concentrate), a gel form or in the form of a dry component, e.g., powder, tablet, lyophilized, or granulated format.

The stored reagent component(s) in the reagent dispensing cap according to the invention are stored in a manner that prevents oxygen or moisture from influencing the chemical or the physical properties of the stored reagent component(s). In one embodiment, a seal cap is provided on one end of the cap to minimize contact between the reagent component(s) stored in the cap and the external environment surrounding the cap. Storage of the reagent component(s) in this manner minimizes loss of the reagent component(s) through evaporation.

The reagent dispensing cap according to the invention is disposed on a container which houses a second reagent component in the form of a liquid, gel or a dry component, e.g., powder, tablet, lyophilized, or granulated format. The contents of the reagent dispensing cap are dispensed into the container to which it is joined by an opening mechanism such as, but not limited to rotating or pushing the cap or a portion of the cap actuated by a plunger such as a ram, to break a seal, such as an elastomeric membrane, between the dispensing cap and container to release the stored component from the cap into the container to which it is joined. Various combinations and arrangements of components in the reagent dispensing cap and components in a container with which the reagent cap component will be mixed are contemplated by the invention.

These and other objects, along with advantages and features of the present invention described herein, will become apparent through references to the following description and the claims. Furthermore, it is to be understood that the features of the various components described herein are not mutually exclusive and can exist in various combinations and permutations.

In one aspect, the invention is directed to a device for storage of and automated dispensing of at least one reagent into a container to be combined with another component in the container to make a diagnostic reagent for use in an automated clinical analyzer, for example, Hemostasis Analyzer, ACLTOP® (Instrumentation Laboratory Company, Bedford, Mass.).

Figure 1C:
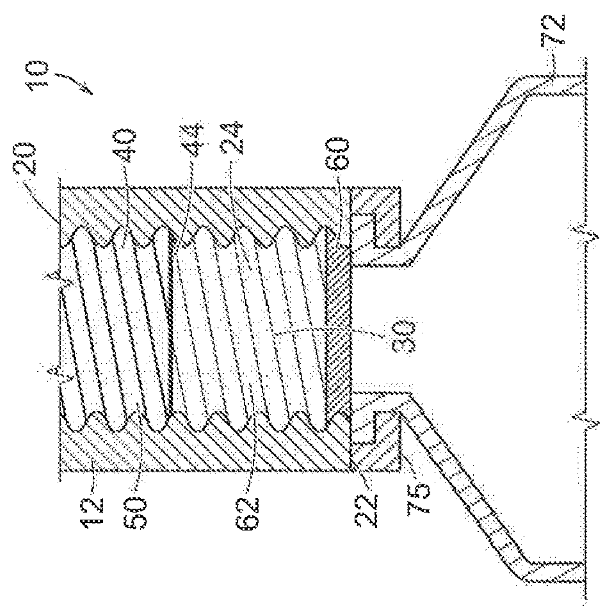
FIG. 1C illustrates a partial transverse section of the housing of the reagent dispensing cap illustrated in FIG. 1A including an exemplary seal joined to the top portion of a container according to an embodiment of the invention.
Figure 1B:
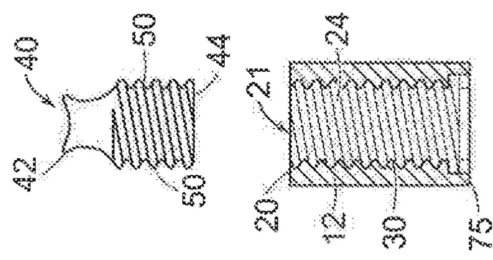
FIG. 1B illustrates a transverse section of an exploded view of the housing and cylindrical member of the reagent dispensing cap illustrated in FIG. 1A according to an embodiment of the invention.
Figure 1A:
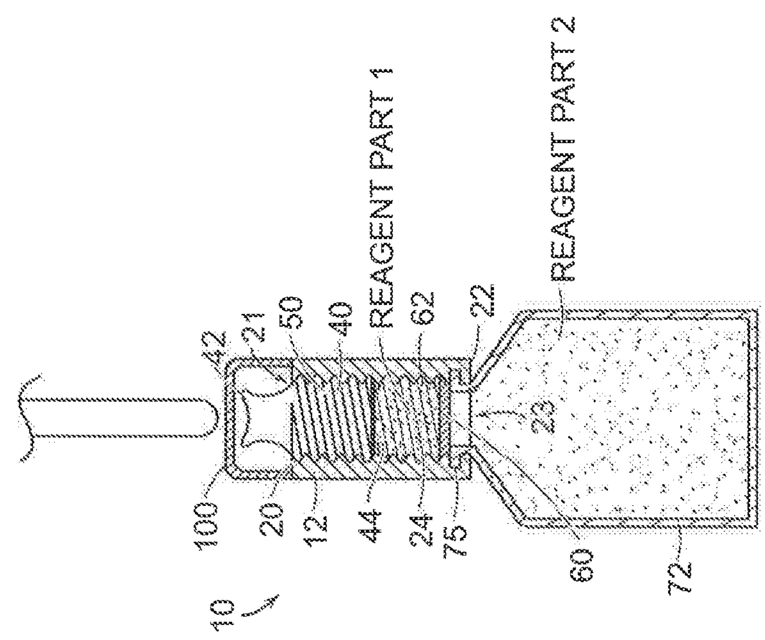
FIG. 1A illustrates a longitudinal transverse section of an exemplary reagent dispensing cap releasably joined to a container according to an embodiment of the invention.

Referring to FIGS. 1A-C, an automated reagent dispensing cap 10 according to the invention includes a cylindrical housing 12 having a first end 20 and an adjacent first opening 21, a second end 22, and an adjacent second opening 23. The housing 12 defines a chamber 62 with a lumen 24 between the first end 20 and second end 22. The chamber 62 may extend from the first end 20 to the second end 22 of the housing 12 or may be confined toward the second end 22 of the housing 12 as described in greater detail below. In one embodiment of the invention, a seal cap 100 is positioned on the first end 20 of the housing 12.

In one embodiment according to the invention, the chamber 62 stores a first reagent component that when mixed with a second reagent component(s) stored in a joined container 72 forms a reagent for a diagnostic assay. The housing 12 further includes internal threads 30 which extend along the interior wall of the housing, preferably but not limited to extending from the first end 20 to the second end 22 of the housing 10.

With continued reference to FIGS. 1A and 1B, in one embodiment of the invention, the reagent dispensing cap 10 further includes a cylindrical member 40 having a long axis and a first end 42 near the first opening 21 of the housing 12 and a second end 44 opposite to the first end 42. The cylindrical member 40 is positioned within the lumen 24 and oriented along the long axis of the housing 12. The cylindrical member 40 includes external threads 50 that are arranged to mate with the internal threads 30 of the housing 12. The cylindrical member 40 is rotatable on or around the internal threads 30 of the housing 12. The mating of the external threads 50 of the cylindrical member 40 with the threads 30 of the housing 12 prevents the reagent contents in the cap 10 from exposure to external elements, such as moisture or oxygen, as well as preventing evaporation of the reagent contents in the housing 12.

Referring to FIGS. 1A-C, the seal cap 100 additionally prevents or minimizes the reagent component(s) in chamber 62 from coming in contact with oxygen or moisture in an external environment surrounding the cap 10. The seal cap 100 also minimizes evaporation of the reagent component(s) in the reagent dispensing cap 10.

As shown in FIG. 1C, in one embodiment of the invention, the reagent dispensing cap 10 further includes a seal 60, such as a frangible membrane positioned at the second end 22 of the chamber 62 of the cylindrical housing 12. The seal 60 prevents the contents of the chamber 62 from mixing with the second reagent component(s) stored in the joined container 72. The space between the second end 44 of the cylindrical member 40 and the seal 60 defines the boundary of the chamber 62 in this embodiment.

Figures 2A, 2B, 2C:
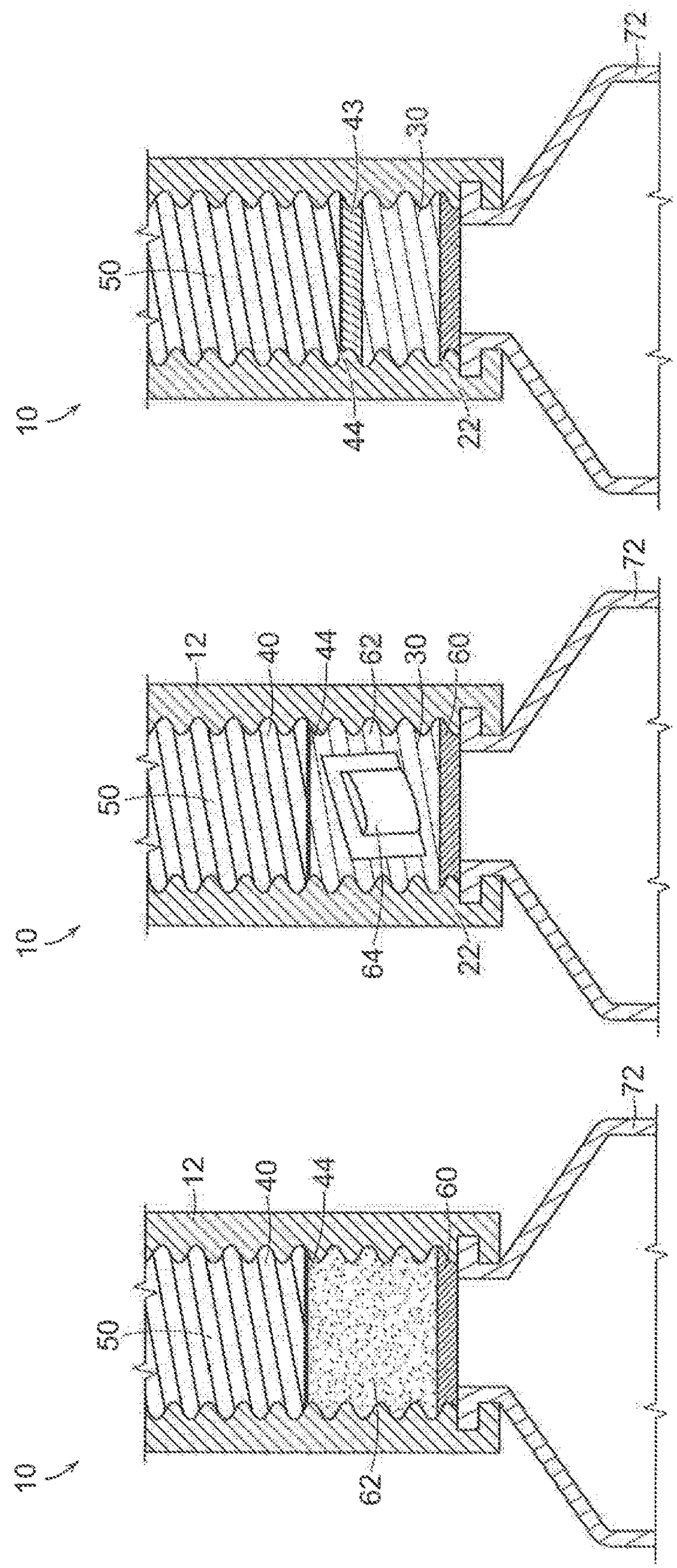
FIG. 2A illustrates a partial transverse section of an exemplary reagent dispensing cap illustrating a first reagent component disposed in a chamber located between the second end of the cylindrical member and a seal according to an embodiment of the invention.
FIG. 2B illustrates a partial transverse section of an exemplary reagent dispensing cap illustrating a blister pack holding a first reagent component disposed in a chamber located between the second end of the cylindrical member and a seal according to an embodiment of the invention.
FIG. 2C illustrates a partial transverse section of an exemplary reagent dispensing cap with the first reagent component distributed on the end of the cylindrical member according to an embodiment of the invention.

As shown in FIG. 2A, in one embodiment, the chamber 62 houses a freely disposed liquid or powdered first component of a reagent. Alternatively, referring now to FIG. 2B, the chamber 62 houses a packet 64 such as a pack, for example a blister pack or ampoule that contains the first reagent component. Alternatively, illustrated in FIG. 2C, the first reagent component is distributed on the second end 44 of the cylindrical member 40, for example, by coating the surface of the second end 44, or enclosing a reagent component in foil 43 joined to the second end 44 of the cylindrical member 40.

Figure 3B:
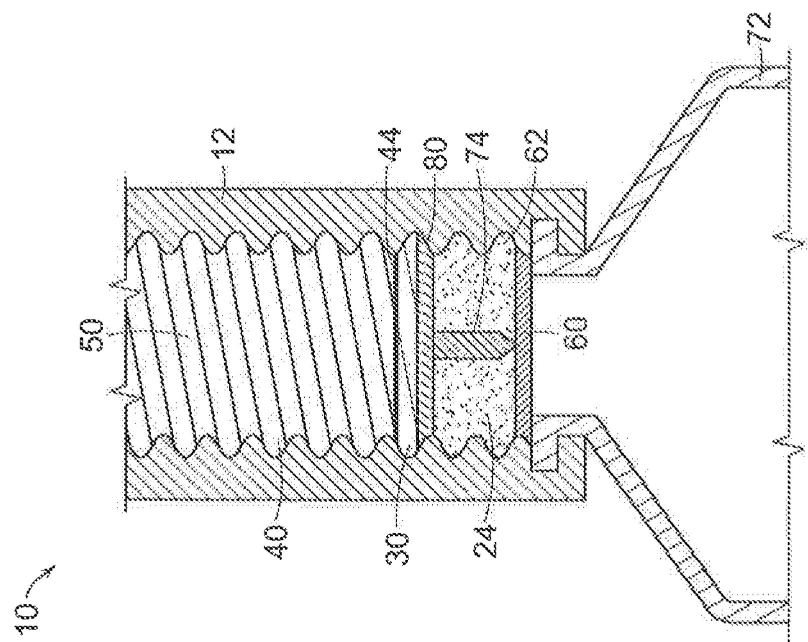
FIG. 3B illustrates a partial transverse section of an exemplary reagent dispensing cap illustrating a first reagent component disposed in a chamber located between a deformable membrane including a needle, and a seal according to an embodiment of the invention.
Figure 3A:
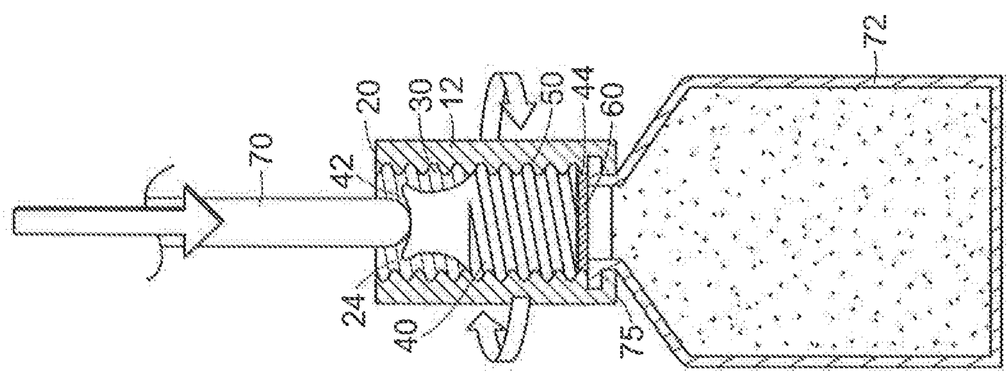
FIG. 3A is a transverse section of a reagent dispensing cap according to the invention illustrating axial rotation of the cylindrical member towards the first reagent component housed between the seal and the second end of the cylindrical member illustrated in FIG. 1A by a ram applied to the first end of the cylindrical member according to an embodiment of the invention.

Referring to FIGS. 3A and 3B, in other embodiments one or more reagent components is distributed in a packet, e.g., a pouch, pill, or bag in the reagent dispensing cap. In the event that the one or more reagent components are stored in a packet, the packet may be ruptured by a piston, e.g., the cylindrical member 40, a piercing probe 74 (e.g., a needle), or by twisting of the reagent dispensing cap 10 (e.g., rotational movement of the cap 10), discussed in greater detail below.

Referring now to FIG. 3A, in one embodiment of the invention, the cylindrical member 40 of the reagent dispensing cap 10 is actuated to rotate axially toward a container 72 to which it is joined, via the mated external threads 50 of the cylindrical member and the internal threads 30 of the housing 12 by applying a ram 70 to the first end 42 of the cylindrical member 40. The cylindrical member 40, as illustrated in FIG. 3A, compresses the contents of the chamber 62 thereby rupturing the seal 60 to release the contents of the chamber 62 into the container 72 where it contacts a second reagent component.

Alternatively, referring to FIG. 3B, chamber 62 for storing a reagent component is bounded by a deformable diaphragm 80 on the side of the chamber 62 towards the second end 44 of the cylindrical member 40 and by the seal 60, e.g., a pierceable membrane on the opposite side of the chamber 62. In one embodiment of the invention, the deformable diaphragm 80 includes a piercing probe 74 comprising a sharp pointed tip (e.g., a needle) that extends axially towards the seal 60.

Figure 4B:
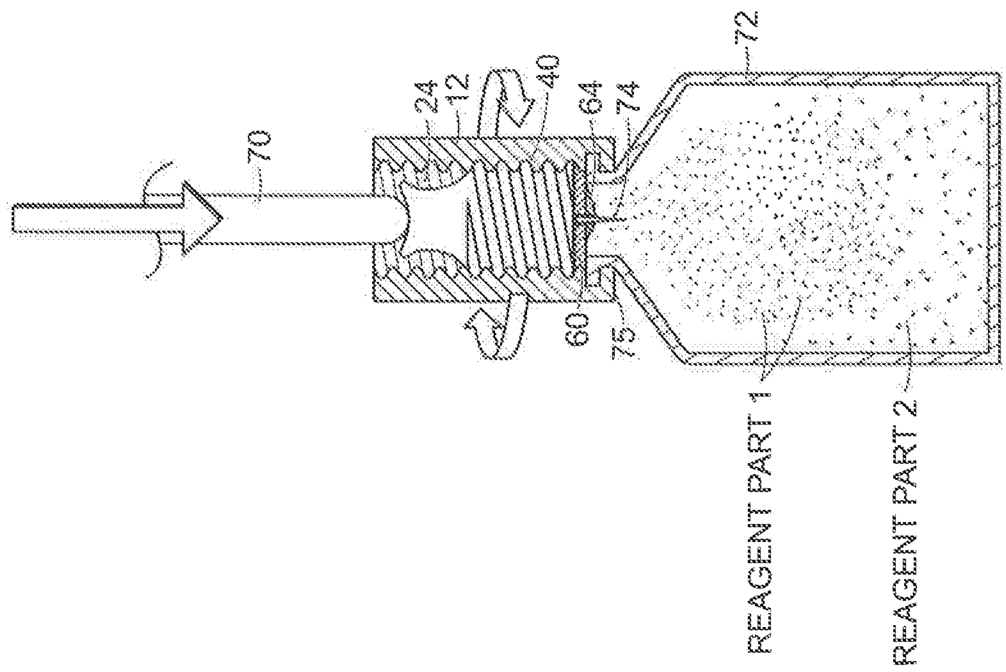
FIG. 4B is a partial transverse section of a reagent dispensing cap according to the invention illustrating axial rotation of the cylindrical member towards the first reagent component housed between the seal and the second end of the cylindrical member illustrated in FIG. 4A by a ram applied to the first end of the cylindrical member according to an embodiment of the invention.
Figure 4A:
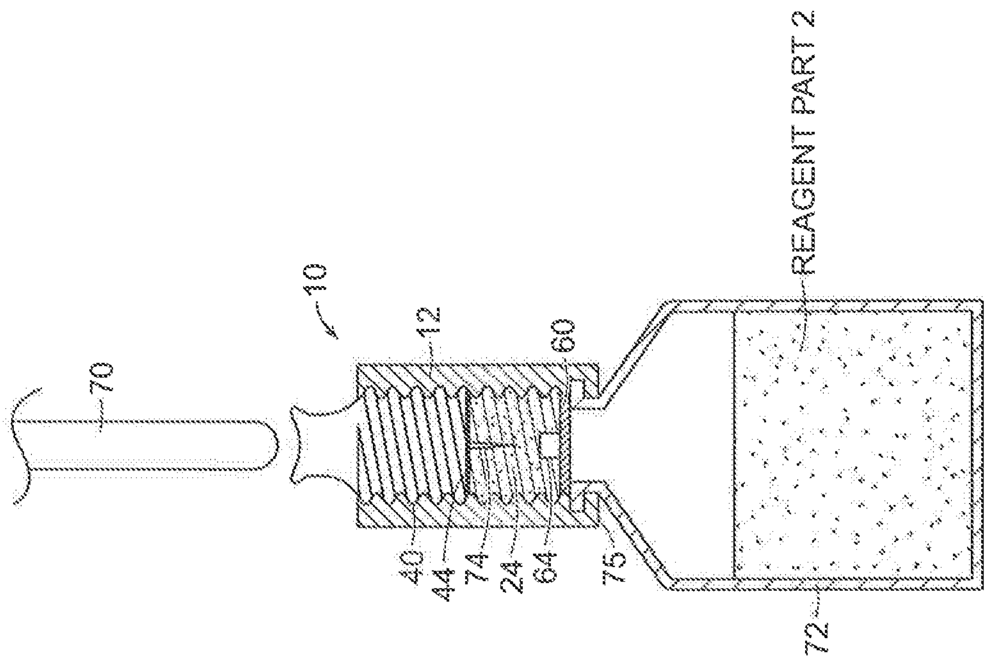
FIG. 4A illustrates a transverse section of an exemplary reagent dispensing cap including a needle axially positioned at the second end of the cylindrical member according to an embodiment of the invention.

In one embodiment of the invention illustrated in FIGS. 4A and 4B, the cylindrical member 40 includes a piercing probe 74 comprising a sharp pointed tip, for example, a needle, axially disposed at the second end 44 of the cylindrical member 40. As the cylindrical member 40 is rotated by the ram 70 towards the seal 60, best illustrated in FIG. 4B, the seal 60, or a packet, e.g., a blister pack or pouch 64 is pierced and its contents released into the container 72 where it is contacted with the second reagent component housed in the container 72.

Figure 5B:
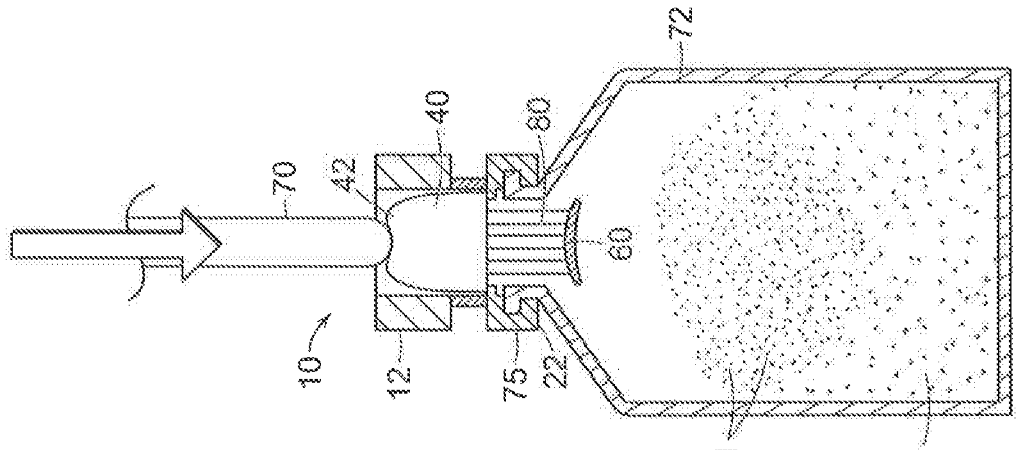
FIG. 5B illustrates actuation of the reagent dispensing cap illustrated in FIG. 5A to dispense the first reagent component into the container by application of a ram to the first end of the cylindrical member to push the opposite end of the cylindrical member into the lumen of the attached container.
Figure 5A:
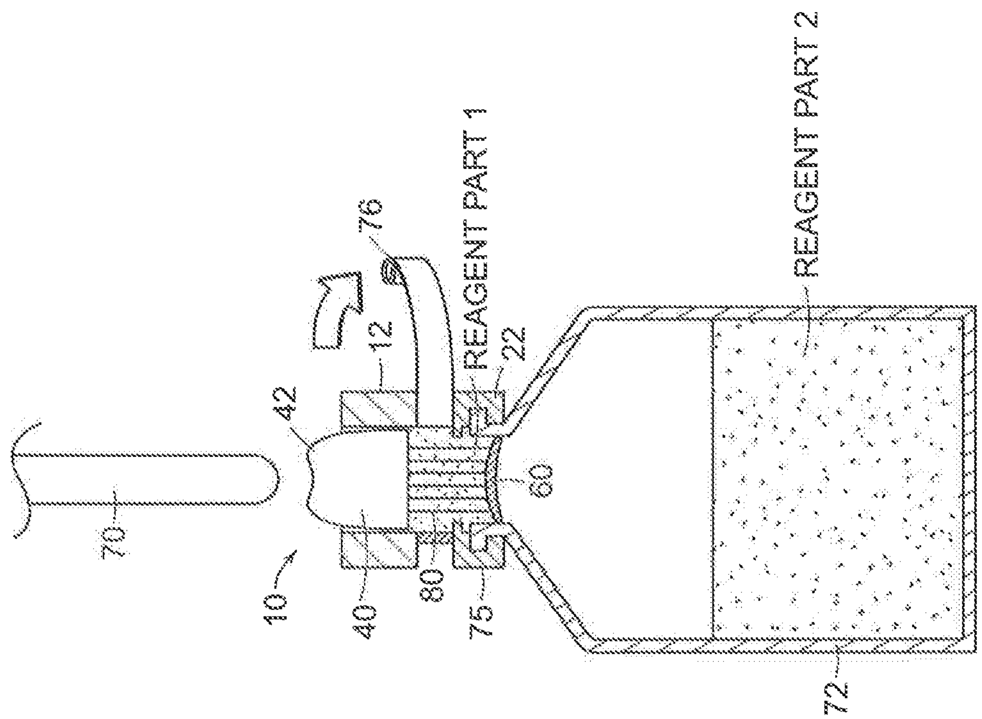
FIG. 5A illustrates another embodiment of the reagent dispensing cap according to the invention including a threadless housing and a threadless cylindrical member.

In yet another embodiment of the reagent dispensing cap 10, referring to FIGS. 5A and 5B, the housing 12 and the cylindrical member 40 are free of threads. In this embodiment, the cylindrical member 40 includes an integral chamber 80 at a portion of the second end 22 of the housing 12. The integral chamber 80 houses the first reagent component. A seal 60 is disposed on the container side of the chamber 80 at the second end 22 of the housing 12. A ram 70 is applied to the first end 42 of the cylindrical member 40 and axially pushes the cylindrical member 40 axially towards the container 72 until the seal 60 of the chamber 80 is introduced into the lumen of the container 72 wherein the contents of the chamber 80 are released and placed in contact with the contents of the container 72.

Figure 6B:
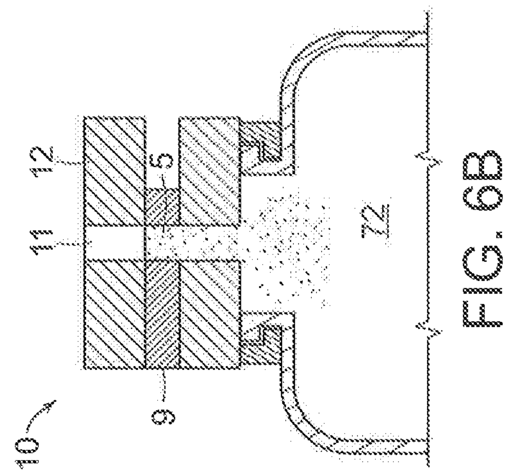
FIG. 6B illustrates actuation of the slider illustrated in FIG. 6A for releasing a first reagent component into the lumen of the attached container.
Figure 6A:
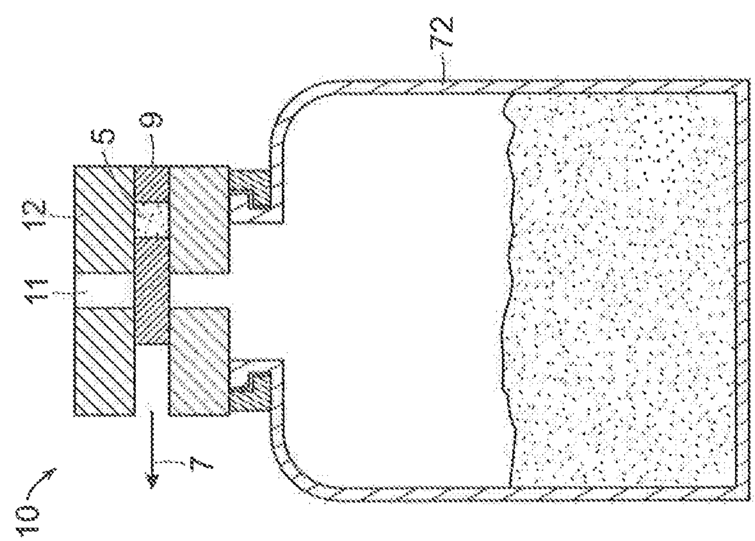
FIG. 6A illustrates yet another embodiment of the reagent dispensing cap according to the invention in which the housing includes a slider.

FIG. 6A-6B illustrates an embodiment of the reagent dispensing cap 10 absent a cylindrical member. Referring to FIG. 6A, reagent dispensing cap 10 in this embodiment, includes a housing 12 with a central axially disposed lumen 11. The housing 12 includes a slider 9, for example, a slideable plug that is capable of moving laterally (arrow 7), i.e., in a direction that is perpendicular to the lumen 11 of the housing 12. The slider 9 may be disc-shaped, rectangular or cylindrical, for example. The slider 9 includes one or more through-holes such as a chamber 5 for housing a reagent component in the reagent dispensing cap 10. The chamber 5 is open on the end of the chamber 5 that faces a container 72 that joins to the reagent dispensing cap 10. Referring to FIG. 6B, the chamber 5 is slideable laterally into the lumen 11 of the housing 12 when the slider 9 is pushed or pulled laterally by an actuator (not shown) in the clinical analyzer. When the chamber 5 is positioned in the lumen 11, the reagent component housed in chamber 5 is released into the container 72 that is joined to the reagent dispensing cap 10 as illustrated in FIG. 6B.

The reagent dispensing cap 10 is reversibly attachable to the container 72. For example, referring again to FIGS. 1A and 1B, the second end 22 of the housing 12 of the reagent dispensing cap 10 includes an attachment device 75 for joining the reagent dispensing cap 10 to the container 72. The attachment piece 75 may be, for example, internal threads on the second end 22 of the housing 12 that mate with external threads on the open end of the container, or a snap-lock, receiving grooves, a friction fit, a Luer lock, or one or more tabs.

A tamper-preventive tear-strip 76, for example, as illustrated in FIG. 5A, may be positioned between the reagent dispensing cap 10 and container 72 to prevent inadvertent activation of the reagent dispensing cap 10.

The present invention provides the advantage of having multi-component reagent storage utilizing a section in the cap 10, e.g., the housing 12, to independently store one or more reagent components in liquid or dry form without exposing the reagent components to moisture or to oxygen that would otherwise alter their chemical or physical properties, or both, and without mixing the reagent components in the cap 10 with the reagent components in the joined container 72. Mixing the stored reagent components in the cap 10 with the reagent components in the joined container 72 when needed provides the additional benefit of reliable results because the reagent components were not pre-mixed and then stored for a longer period of time that would result in reagent deterioration.

Storage of one or more reagent components in a section of the cap 10, e.g., the housing 12, prior to its automated dispensing into the joined container 72 minimizes evaporation of the components in the housing 10 and in the joined container 72. Accidental human intervention is minimized because the release and the mixing of reagent components separately stored in the housing 12 and the container 72 is automated. The invention described herein minimizes errors in analytical results caused by prolonged storage and degradation of a prepared reagent, and the accidental loss of reagent components caused by human intervention. These features add to the cost-effectiveness of the reagents and the analysis of a patient sample.

EXEMPLIFICATIONS

An Exemplary Dual Chamber Reagent Mixing Container for Hemostasis Testing in an Automated Clinical Hemostasis Analyzer Instrument A specific non-limiting example of the reagent dispensing cap according to the invention described above is a reagent dispensing cap for prothrombin time (PT) testing by an automated hemostasis analyzer instrument. The reagent for PT testing contains two components: a diluent and a concentrated PT reagent. The volume ratio between the diluent and the PT reagent is 19:1. Each PT test requires 100l diluted PT reagent. A reagent dispensing cap useful for PT tests in an automated clinical analyzer would generally require between about 500 to about 1000 PT tests. A 1000 PT test reagent dispensing cap requires about 100 ml of diluted PT reagent, namely 95 ml diluent and 5 ml concentrated PT reagent. In the exemplary reagent cap disclosed herein, for example the reagent cap and container illustrated in FIG. 1, the container 72 into which the reagent dispensing cap empties would have a volume capacity greater than 100 ml and would initially contain 95 ml of diluent. The chamber of the reagent cap would contain 5 ml of concentrated PT reagent. Upon actuation by the cylindrical member described in the above embodiments, the 5 ml of concentrated PT reagent is introduced into the container and contacts the second reagent component held in the container 72. A self-contained PT reagent dispensing cap 10 with automated reagent preparation, sustainable for about 1000 PT assays, is therefore achieved.

An Exemplary Dual Chamber Reagent Mixing Container for Analyte Testing in an Automated Clinical Analyzer A second non-limiting example of the reagent dispensing cap according to the invention is a dispensing cap for a hemostasis quality control (QC) reagent, for example. A specifically prepared, lyophilized plasma sample with known analytical testing results would serve as a QC reagent. The QC reagent is stored in the container to which the reagent dispensing cap is joined. De-ionized water is stored in the chamber of the reagent dispensing cap. Prior to use, the deionized water is introduced from the chamber in the reagent dispensing cap into the container holding the lyophilized QC reagent.

What is claimed is:

1. A device for storing reagent components in an automated clinical analyzer, comprising:

a container lid, said container lid comprising, a cylindrical wall about a longitudinal central axis, the cylindrical wall defining a lumen, a first opening to the lumen at a first end of the cylindrical wall, a second opening to the lumen at a second end of the cylindrical wall a portion of the lumen defining a reagent chamber 62 configured to store one or more reagents, wherein the cylindrical wall further comprises internal threads 30 extending from the first end 20 to the second end 22 of the cylindrical wall;

a cylindrical member 40 positioned within the lumen and confined between and shorter than the distance between the first and second ends, said cylindrical member 40 comprising external threads 50 configured to operatively engage the internal threads 30 of said cylindrical wall and thereby to move the cylindrical member along the central longitudinal axis within the lumen, and wherein said engagement between the internal threads 30 and said external threads 50 form a gas-tight seal between the first opening of the lumen and the reagent chamber 62;

a breakable seal 60 positioned at the second end 22 of cylindrical wall extending across the second opening of the lumen, wherein the reagent chamber 62 is bounded by the cylindrical wall, the cylindrical member 40 and the breakable seal 60; and an attachment structure 75 joined to the second end of the cylindrical wall, the attachment structure 75 including an engagement portion shaped for receiving a mating engagement portion of a container 72 at an opening of the container 72 and retaining the cylindrical wall and the breakable seal 60 in a fixed position against the container 72 such that the breakable seal 60 seals the opening of the container 72.

2. The device of claim 1, wherein said attachment structure 75 is selected from the group consisting of threads, snap-lock, mating rings, receiving grooves, a friction-fit mechanism, Luer lock, and one or more tabs.

3. The device of claim 1, further comprising; a cap 100 positioned at the first end 20 of the cylindrical wall, the cap 100 enclosing the cylindrical member and sealing the first opening of the lumen.

4. The device of claim 3, wherein said cap 10 is configured to reversibly attach to the container 72.

5. The device of claim 1, further comprising;

the container 72 coupled to the container lid via the attachment structure 75.

6. The device of claim 5, further comprising:

a first reagent stored in the reagent chamber of the container lid; and a second reagent separately stored in the container, wherein the first reagent and the second reagent are separated from each other by the breakable seal 60.

7. The device of claim 6, wherein the first reagent is capable of breaking the breakable seal and mixing with the second reagent in response to displacement of the cylindrical member along the longitudinal axis toward the breakable seal.

8. The device of claim 1, further comprising a piercing probe extending from the cylindrical member toward the breakable seal, the piercing probe including a pointed tip configured for piercing the breakable seal in response to displacement of the cylindrical member along the longitudinal axis toward the breakable seal.

* * * * *